United States Patent
Palti et al.

(10) Patent No.: US 6,517,494 B2
(45) Date of Patent: Feb. 11, 2003

(54) SYSTEM FOR MEASURING BLOOD PRESSURE

(75) Inventors: Yoram Palti, Haifa (IL); Yoram Wasserman, Haifa (IL); Baruch Glick, Haifa (IL); Israel Urbach, Haifa (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 34 days.

(21) Appl. No.: 09/878,680

(22) Filed: Jun. 11, 2001

(65) Prior Publication Data

US 2001/0056242 A1 Dec. 27, 2001

(30) Foreign Application Priority Data

Jun. 16, 2000 (EP) .............................. 00202086

(51) Int. Cl.[7] ................................. A61B 5/02
(52) U.S. Cl. ...................... 600/493; 600/495; 600/496; 600/490
(58) Field of Search ................. 600/493–496, 600/490, 485

(56) References Cited

U.S. PATENT DOCUMENTS

| | | | |
|---|---|---|---|
| 4,660,566 A | 4/1987 | Palti | 128/677 |
| 4,889,132 A | * 12/1989 | Hutcheson et al. | 600/481 |
| 5,564,426 A | 10/1996 | Iwai | |
| 5,993,396 A | 11/1999 | Friedman et al. | |

\* cited by examiner

*Primary Examiner*—Gregory Huson
*Assistant Examiner*—Amanda Flynn
(74) *Attorney, Agent, or Firm*—Ernestine Bartlett

(57) ABSTRACT

A system (1) for measuring blood pressure during a limited number of blood pressure cycles at an area (2) overlying an artery (3) of a living subject, comprising a mechanism (4) for applying a pressure (P) to the artery for occluding artery in response to a pressure signal (Uprise), and for subsequently releasing said pressure to re-open artery in response to a pressure release signal (Uprelease), and a mechanism (11) for computing, by comparing a first time duration ($\Delta T1$) with a second time duration ($\Delta T2$), a delay time (Tdelay1) from a reference point in time after which a next pressure release signal is to be supplied to a mechanism (4) for applying a pressure, and for computing a pressure (P2) to be applied to artery in a next measuring cycle, and for supplying subsequently a pressure signal (Uprise) and a pressure release signal (Uprelease) corresponding to computed pressure (P2) and delay time (Tdelay1) to a mechanism (4) for applying a pressure.

7 Claims, 5 Drawing Sheets

SYSTEM FOR MEASURING BLOOD PRESSURE

Figure 1:
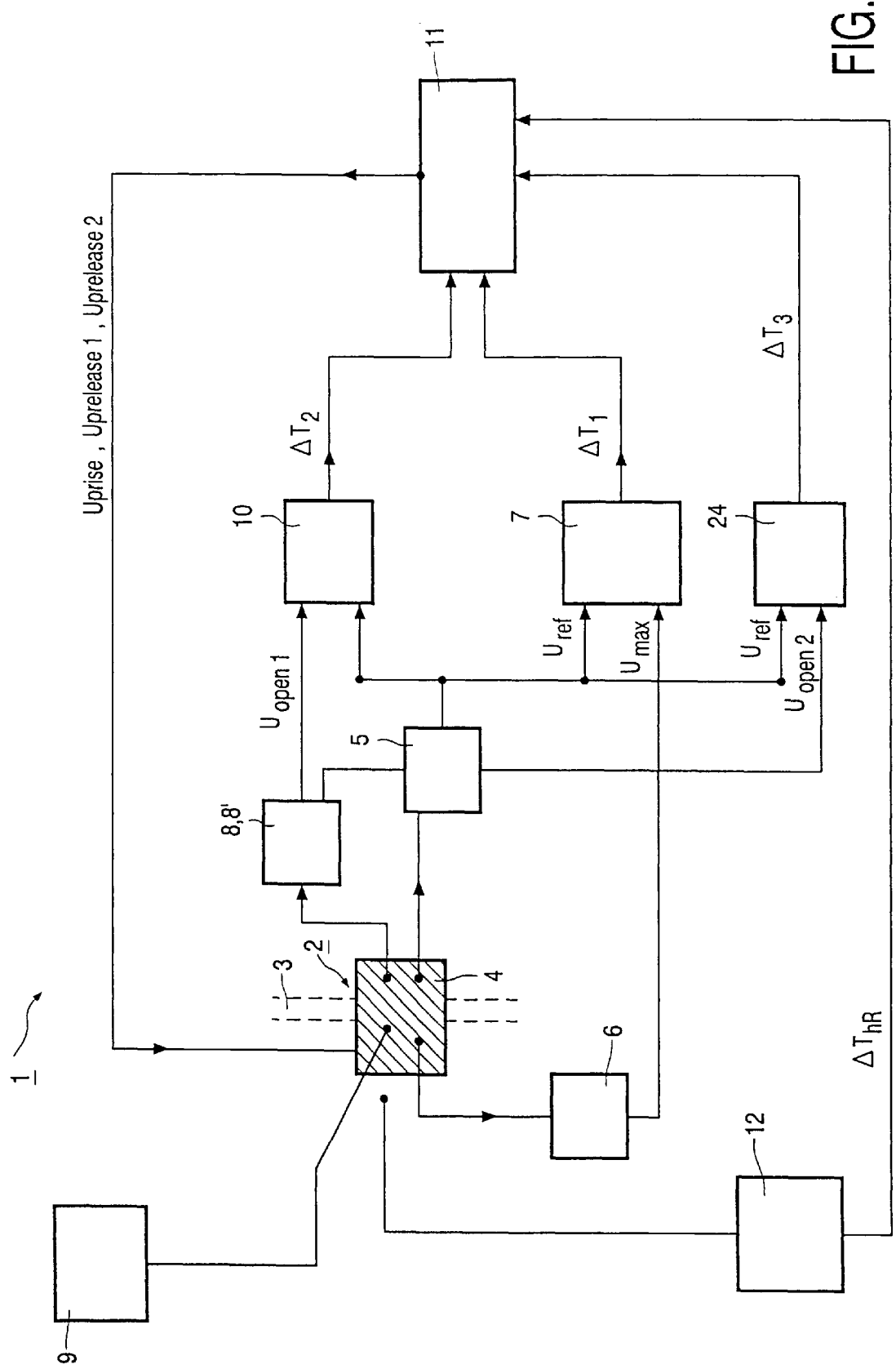

The invention relates to a system for measuring blood pressure during a limited number of blood pressure cycles at an area overlying an artery of a living subject.

A system of the type defined in the opening paragraph is known from U.S. Pat. No. 4,660,566.

The known system comprises a measuring unit comprising a sensor provided on an inflatable cushion, and a processing unit. The cushion is provided on a carrier comprising a bracelet of flexible material worn by a user around his or her wrist. In this known system, pressure pulses are applied by means of the cushion to a local, discrete external point overlying the radial artery of the subject, to effect a blocking and successively an unblocking condition of the artery, or to effect an unblocking and successively a blocking condition of the artery. When the sensor detects said respective unblocking or blocking condition, the instantaneous value of the pressure in the cushion is measured for the purpose of providing through the processing unit a value of said subject's blood pressure. A disadvantage of the known system is that the measurement results of the systolic and diastolic blood pressure given by the system are not accurate due to the fact that the measurements along the subjects pressure line cannot be exactly located, and it is not known whether there is at least one measurement at the systolic peak and one at the diastolic minimum of the blood pressure cycle. Because of this, long measurement times are needed in order to have a high statistical probability that the measurements have taken place at those points in time at which the systolic and the diastolic pressure occurred.

It is an object of the invention to provide an improved system for measuring blood pressure which offers a more accurate and faster measurement of systolic and diastolic blood pressures.

To achieve this object, a system according to the invention is characterized in that it comprises:

means for applying a pressure to the artery for occluding said artery in response to a pressure signal and for subsequently releasing said pressure to re-open said artery in response to a pressure release signal;

means for determining a reference point in time, and for providing a reference time signal corresponding to said reference point in time, means for detecting a first point in time at which a maximum pressure occurs during a blood pressure cycle, and for providing a first time signal corresponding to said first point in time;

means for computing, from the reference time signal and the first time signal, a first time duration from the reference point in time to the first point in time;

means for detecting a second point in time at which an opening of the artery occurs after the release of said pressure, and for providing a second time signal corresponding to said second point in time;

means for determining the pressure in said means for applying pressure to the artery, at the second point in time;

means for computing, from the reference time signal and the second time signal, a second time duration from the reference point to the second point in time;

means for computing, by comparing the first time duration with the second time duration, a delay time from said reference point in time after which a next pressure release signal is to be supplied to said means for applying a pressure, and for computing a pressure to be applied to said artery in a next measuring cycle, and for supplying subsequently a pressure signal and a pressure release signal corresponding to said computed pressure and delay time to said means for applying a pressure.

The measurement of blood pressure is started by applying a pressure to the artery, until the artery is occluded by said pressure. After that, the reference point in time is determined, from which point in time the pressure in the cushion is subsequently released until the artery re-opens. During this release of pressure, the point in time at which the maximum pressure occurs is detected, and the point in time at which the opening of the artery occurs is detected, and a first and a second time signal corresponding to these respective points in time are provided. The pressure in the pressure applying means which indicates the blood pressure in the artery is determined at the second point in time, being the time of the opening of the artery. The first time duration from the reference point in time to the point in time at which the maximum pressure occurs is then compared with the second time duration from the reference point in time to the point in time at which the opening of the artery occurs. From this comparison the delay time is computed. This delay time is the delay time from the reference point in time, after which a next pressure release signal is supplied to the means for applying the pressure. Furthermore, the pressure to be applied to said artery in a next measuring cycle is computed in dependence on this comparison. Signals, which correspond, to this computed delay time and pressure are then supplied to the means for applying a pressure to the artery. The delay time and the pressure for the pressure applying means are refined by repeating this measurement a limited number of cycles. The comparison of the first time duration with the second time duration is thus repeated until the point in time at which the opening of the artery coincides with the point in time at which the maximum pressure occurs within a pretermined tolerance time interval. The pressure determined in the pressure applying means at this moment gives an accurate indication of the systolic blood pressure of the subject. In this way the systolic blood pressure is derived with accuracy and in a fast manner.

An embodiment of a system in accordance with the invention is characterized in that the reference point in time is a point in time at which a start of a systolic phase in a blood pressure cycle occurs. The measurement starts at a point in time which corresponds to the start of the rise in blood pressure in the artery, and thus the measured pressures are known to be in the vicinity of the maximum pressure, which is the systolic blood pressure. This is advantageous for increasing the speed with which the systolic blood pressure is measured, because only a limited number of measurements is needed for determining the systolic blood pressure.

An embodiment of a system in accordance with the invention is characterized in that the means for detecting the start of said systolic phase comprise a sensor for detecting during operation a point in time at which a pressure pulse in the means for applying a pressure to the artery rises above a predetermined threshold value. The start of the systolic phase is thus determined in an easy manner.

An embodiment of a system in accordance with the invention is characterized in that it comprises said means for computing, which are furthermore designed for determining a further delay time from said reference point in time after which a further pressure release signal is to be supplied to said means for applying a pressure in a next measuring step for measuring the diastolic blood pressure and for supplying a further pressure release signal corresponding to said further delay time, means for determining, from the timing of at least two heart beats of the subject, a heart rate duration from the reference point in time to an end point in time corresponding to an end of one pressure cycle, means for detecting a further point in time at which an opening of the artery occurs after the release of said pressure in response to said further pressure release signal, and for providing a third time signal corresponding to said further point in time, means for computing, from the reference time signal and the further time signal, a third time duration from the reference point in time to the further point in time, said means for computing further determining, by comparing the heart rate duration and the third time duration, a next value for said further delay time after which a next pressure release signal is to be supplied to said means for applying a pressure in said next measuring step, and for supplying subsequently a next value for said further pressure release signal corresponding to said next value for said further delay time to said means for applying a pressure.

For determining the diastolic pressure, a further delay time from said reference point in time, after which a further pressure release signal is to be supplied to said means for applying a pressure, is determined in a next measuring step. A further pressure release signal corresponding to said further delay time is then supplied to the means for applying a pressure, and the pressure in the cushion is subsequently released until the artery re-opens. During this release of pressure, the point in time at which the opening of the artery occurs is detected, and a third time signal corresponding to this point in time is provided. Next to this, a heart rate duration from the reference point in time to an end point in time corresponding to an end of one pressure cycle is determined from the timing of at least two heart beats. This heart rate duration and this third time duration are compared. This comparison provides a next value for the further delay time. A signal which corresponds to this computed next value for the further delay time is then supplied to the means for applying a pressure to the artery. The following next values for the further delay time for the pressure applying means are refined by repeating this measurement a limited number of cycles. The comparison of the heart rate duration with the third time duration is thus repeated until the point in time at which the opening of the artery coincides within a predetermined tolerance time interval with the point in time at which the blood pressure cycle ends, this being the point in time at which the minimum pressure occurs. The pressure determined in the pressure applying means at this moment gives an accurate indication of the diastolic blood pressure of the subject. In this way the diastolic blood pressure is derived with accuracy and in a fast manner.

An embodiment of a system in accordance with the invention is characterized in that said means for detecting said first point in time comprise a pressure sensor for measuring a pressure in the means for applying a pressure to the artery during operation, and a processor for determining said first point in time from a signal provided by the pressure sensor. The pressure sensor measures the pressure in the means for applying a pressure to the artery and provides a signal to the processor in response to this. The processor then determines said first point in time from this signal. In this way the first point in time is determined in a simple manner.

An embodiment of a system in accordance with the invention is characterized in that the means for detecting said second point in time comprise an electro-optical sensor for detecting the presence of blood in the artery and a further processor for determining said second point in time from a signal provided by the electro-optical sensor. The electro-optical sensor is placed near the artery and detects the presence of blood in the artery by checking the absorption of light emitted by the sensor. When the artery opens, blood enters the artery which absorbs said light. The electro-optical sensor detects this change in the absorption of light, and provides a signal to the processor in response to this. The processor then determines said second point in time from this signal.

An embodiment of a system in accordance with the invention is characterized in that said means for computing also determine a pressure-time profile according to which said pressure is released, said means for computing supplying a pressure release signal corresponding to said profile. The pressure-time profile of releasing the pressure in the means for applying pressure can be adjusted in this manner within a limited number of measuring cycles so as to achieve an accurate measurement. Thus a smaller number of measuring cycles is needed, and a faster measurement is achieved.

Figure 2A:
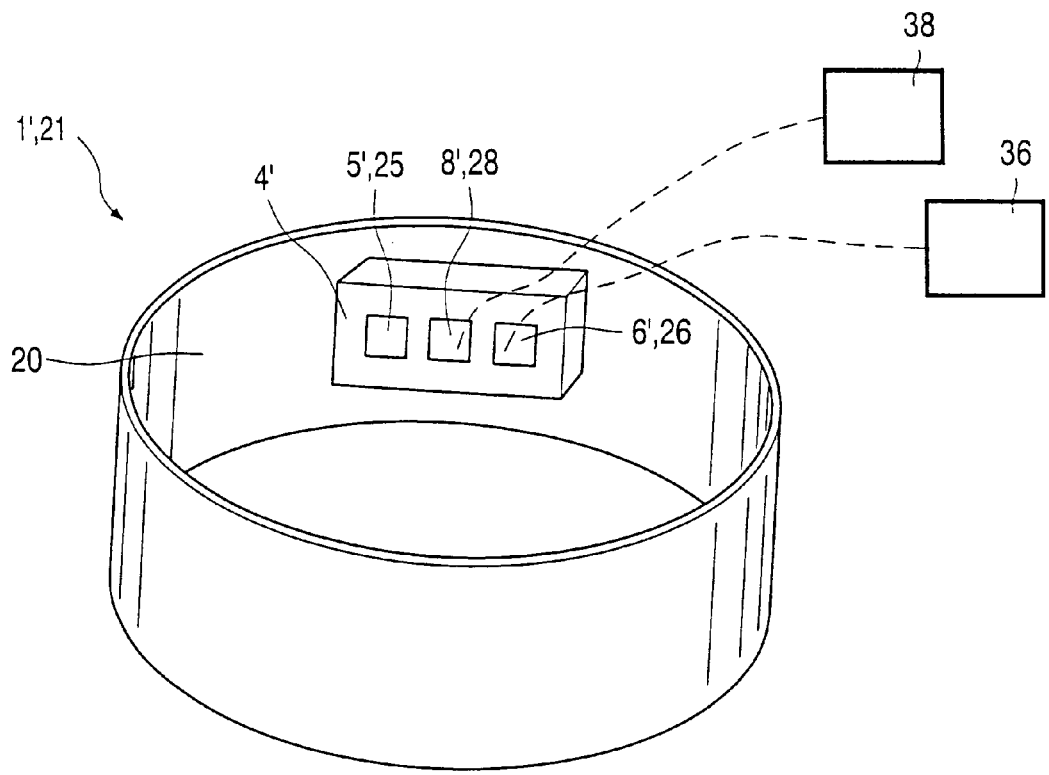
Figure 2B:
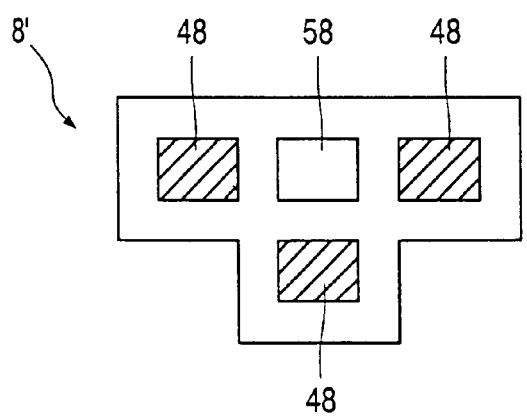
Figure 3A:
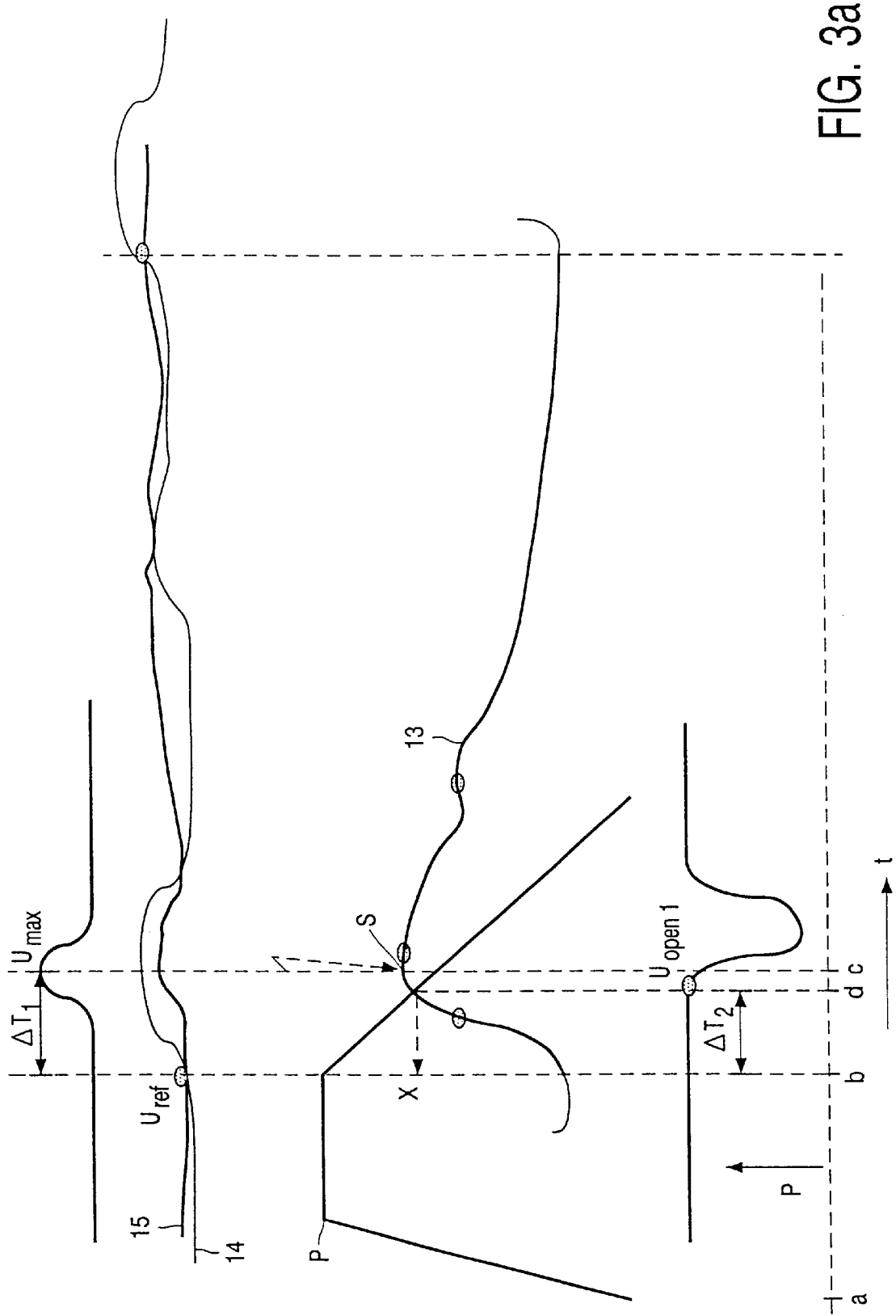
Figure 3B:
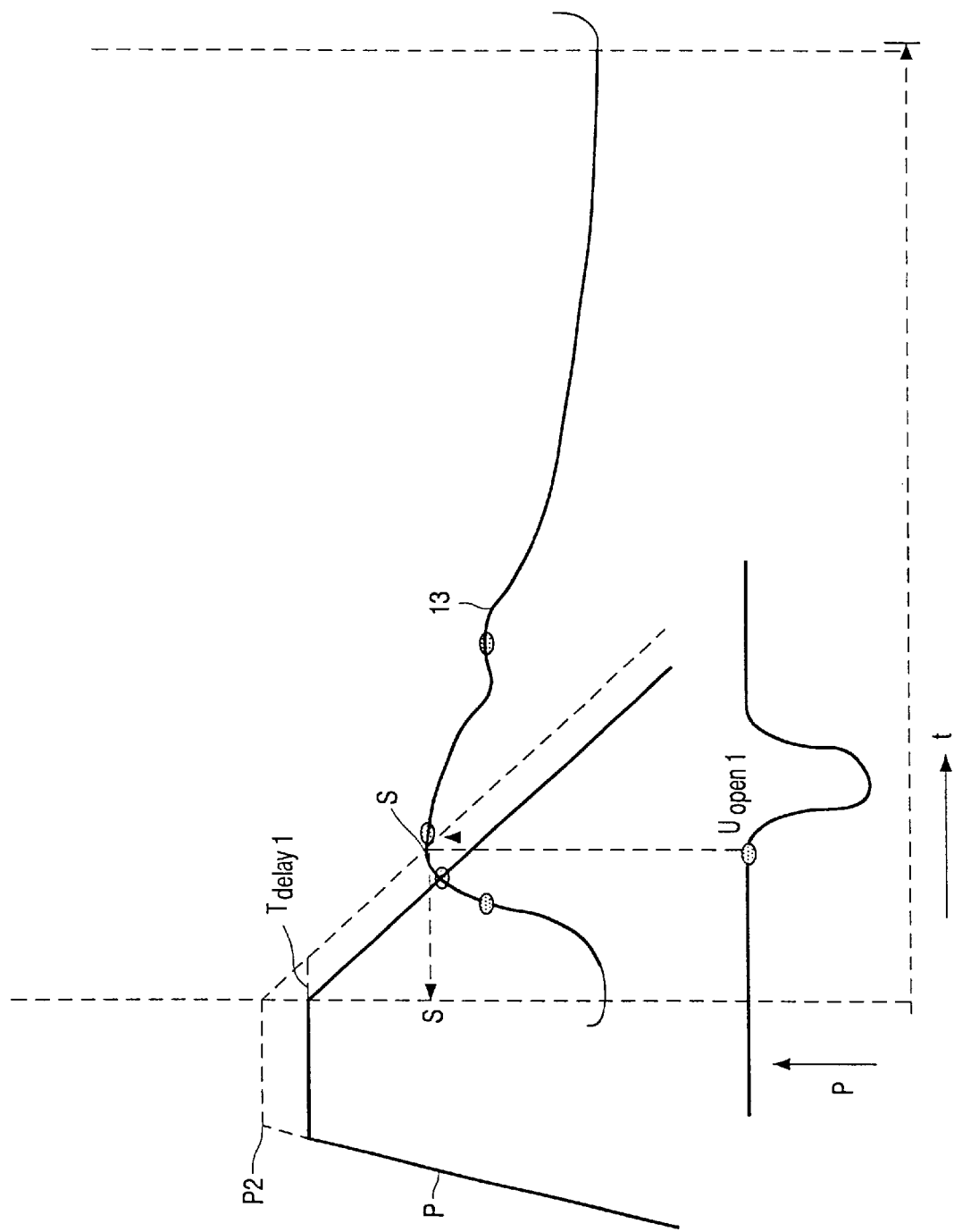
Figure 4:
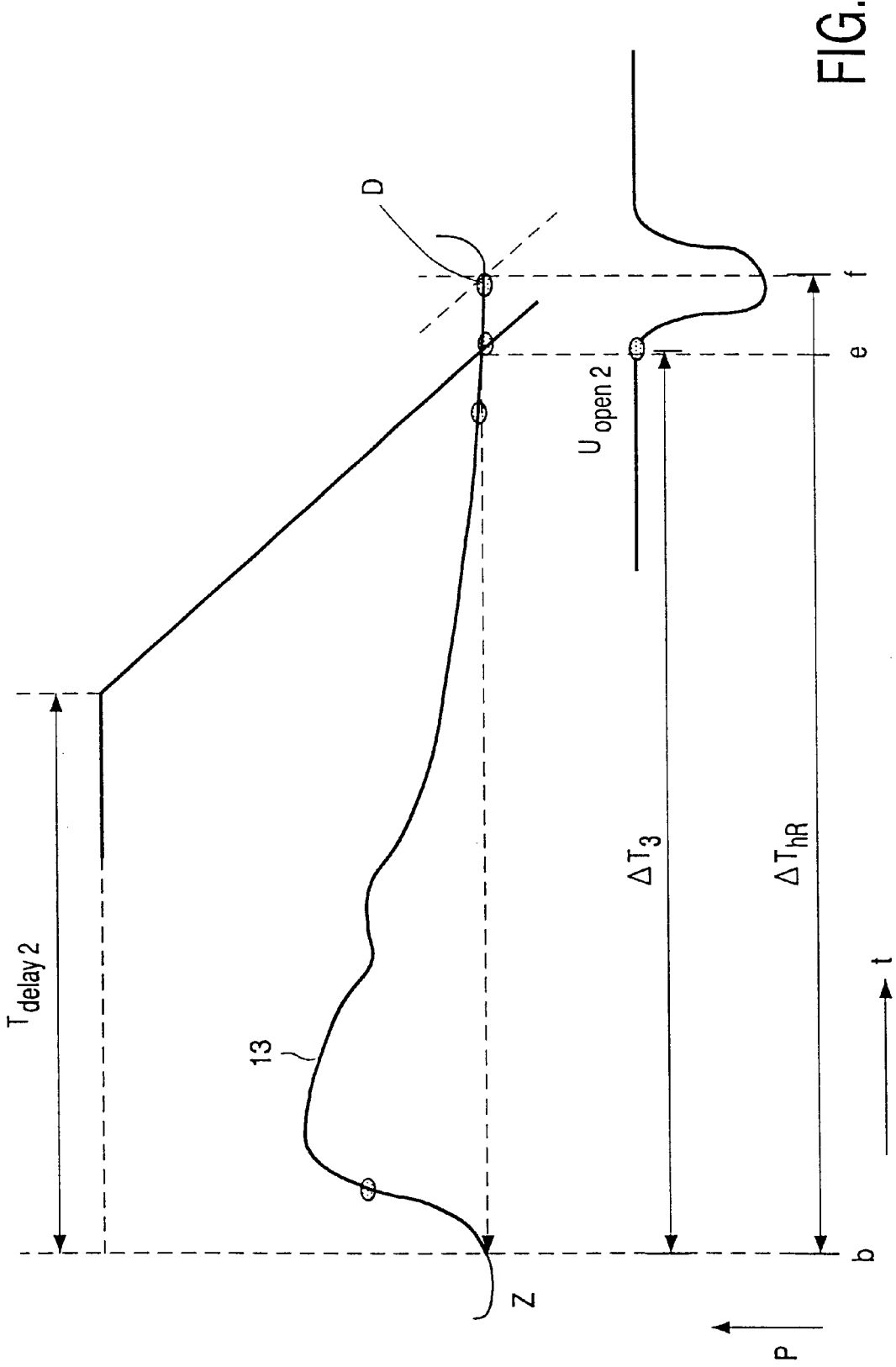

The invention will be described in more detail hereinafter with reference to the drawings, in which FIG. 1 shows in functional blocks a first embodiment of a system according to the invention, FIG. 2a is a perspective view of a device comprising the system of FIG. 1, FIG. 2b diagrammatically shows a sensor of the device of FIG. 2a, FIG. 3a is a diagram of a measurement of the systolic blood pressure with the system of FIG. 1 in a first measurement cycle, FIG. 3b is the diagram of the measurement of FIG. 3a after a number of cycles, FIG. 4 is a diagram of a measurement of the diastolic blood pressure with the system of FIG. 1 in a further measuring step.

FIG. 1 shows a system 1 for measuring blood pressure during a limited number of blood pressure cycles at an area 2 overlying an artery 3 of a living subject. The system 1 comprises means 4 for applying a pressure P to the artery 3 for occluding said artery 3 in response to a pressure signal Uprise, and for subsequently releasing said pressure to reopen said artery 3 in response to a pressure release signal Uprelease. The means 4 for applying pressure comprise, for example, an airbag which can be inflated and deflated, but alternative types of pressure applying means are also possible. The system 1 further comprises means 5 for determining a reference point in time and for providing a reference time signal Uref corresponding to said reference point in time. It further comprises means 6 for detecting a first point in time at which a maximum pressure occurs during a blood pressure cycle and for providing a first time signal Umax corresponding to said first point in time. It further comprises means 7 for computing, from the reference time signal Uref and the first time signal Umax, a first time duration $\Delta T1$ from the reference point in time to the first point in time. It further comprises means 8 for detecting a second point in time at which an opening of the artery 3 occurs after the release of said pressure and for providing a second time signal Uopen1 corresponding to said second point in time, and means 9 for determining the pressure in said means for applying pressure to the artery 3 at the second point in time. The system further comprises means 10 for computing, from the reference time signal Uref and the second time signal Uopen1, a second time duration $\Delta T2$ from the reference point to the second point in time. It further comprises means 11 for computing, by comparing the first time duration ΔT1 with the second time duration ΔT2, a delay time Tdelay1 from said reference point in time after which a next pressure release signal is to be supplied to said means 4 for applying a pressure, and for computing a pressure P2 to be applied to said artery 3 in a next measuring cycle, and for supplying subsequently a pressure signal Uprise and a pressure release signal Uprelease corresponding to said computed pressure P2 and delay time Tdelay1 to said means 4 for applying a pressure. Means 11 for computing further determine, by comparing the heart rate duration ΔThr and the third time duration ΔT3, a next value for a further delay time Tdelay2 after which a next pressure release signal is to be supplied to said means 4 for applying a pressure in said next measuring step, and for supplying subsequently a next value for said further pressure release signal Uprelease2 corresponding to said next value for said further delay time Tdelay2 to said means 4 for applying a pressure. Said means 11 for computing also determine a pressure-time profile according to which said pressure is released, said means 11 for computing supplying a pressure release signal Uprelease corresponding to said profile.

FIG. 2a shows a device comprising the system of FIG. 1. The system 1' is incorporated in a wrist blood pressure monitor 21 comprising a band 20, on which a pressure applying means 4' is provided, here formed by an inflatable and deflatable airbag. In this embodiment, said means 5 for determining a reference point in time and for providing a reference time signal Uref corresponding to said reference point in time comprise means 5' for detecting the start of a systolic phase in a blood pressure cycle. These means 5' comprise a sensor 25 for detecting during operation a point in time at which a pressure pulse 14 in the means 4' for applying a pressure to the artery rises above a predetermined threshold value 15. This will be further shown in FIG. 3. In this embodiment, furthermore, said means 6' for detecting said first point in time comprise a pressure sensor 26 for measuring a pressure in the means 4' for applying a pressure to the artery 3 during operation, as well as a processor 36 for determining said first point in time from a signal provided by the pressure sensor 26.

In this embodiment, furthermore, said means 8' for detecting said second point in time comprise an electro-optical sensor 28 for detecting the presence of blood in the artery and a further processor 38 for determining said second point in time from a signal provided by the electro-optical sensor 28. The electro-optical sensor 28 in this embodiment comprises a configuration of electro-optical detectors 48 with a light source 58, for example a Light Emitting Diode. During operation, the light source 58 emits light to the area overlying the artery. When the artery is firstly closed by the pressure applying means 4', the area overlying said artery reflects a certain amount of the light coming from the light source 58. When the pressure in the pressure applying means 4' is released in response to a pressure release signal, said artery re-opens and blood enters the artery again. A change in the reflection of light by said area occurs because the blood present in the artery absorbs a certain amount of the light. The electro-optical detectors 48 detect this change and provide a signal to the processor 38 signal according to it. The processor 38 then determines said second point in time, being the point in time at which an opening of the artery occurs.

FIG. 3a shows a diagram of a measurement of the systolic blood pressure with the system of FIG. 1 in a first measurement cycle. In the diagram, a time t and a pressure P, being the pressure in the pressure applying means 4, are plotted against each other. A blood pressure wave 13 is also shown in the diagram. As can be seen in FIG. 3a, the pressure P in the pressure applying means 4' is increased to a first level at a point in time a, at which the artery is occluded by the pressure applying means 4'. The pressure P in the pressure applying means 4' is subsequently released to re-open the artery at a certain point in time. The pressure in the pressure applying means will equal the pressure in the artery at some point in time during this release, which can be seen in the diagram at the intersection of P and the blood pressure wave 13. At this point, the pressure X in the artery is determined. However, as can be seen in the diagram, this pressure X determined in the artery in this measurement does not represent the systolic blood pressure S, but a pressure lower than this, since its measurement took place before the occurrence of the systolic blood pressure S. In a next measuring cycle, therefore, the pressure P in the pressure applying means 4' is increased to the level at which the artery is occluded by the pressure applying means 4'. At a further point in time b, a reference point in time is determined by means 5', and a reference time signal Uref is provided corresponding to said reference point in time. The reference point in time in this embodiment is a point in time at which a start of a systolic phase in the blood pressure cycle occurs. This start of the systolic phase is detected by the sensor 25, which detects the point in time at which the pressure pulse 14 in the pressure applying means 4' rises above the predetermined threshold value 15. This point in time is indicative of the start of the systolic phase. From this point in time b, the pressure P in the pressure applying means 4' is subsequently released to re-open the artery. The pressure sensor 26 measures the pressure in the pressure applying means 4' during this release, and the processor 36 determines a first point in time c at which a maximum pressure occurs from a signal provided by the pressure sensor 26. A first time signal Umax is provided corresponding to this point in time. A first time duration ΔT1 from the reference point in time b to the first point in time c is computed from the reference signal Uref and the first time signal Umax. Next to this, the electro-optical sensor 28 of means 8' detects the presence of blood in the artery 3 when the artery opens, and the further processor 38 determines a second point in time d at which the opening of the artery 3 occurs from a signal provided by the electro-optical sensor 28. Corresponding to this point in time d, a second time signal Uopen1 is provided. A second time duration ΔT2 from the reference point in time b to the second point in time d is computed from the reference time signal Uref and the second time signal Uopen1.

A comparison of the first time duration ΔT1 and the second time duration ΔT2 serves to compute a delay time Tdelay1 from said reference point in time b after which a next pressure release signal is to be supplied to said means 4' for applying a pressure and a pressure P2 to be applied to said artery in a next measuring cycle. A pressure signal Uprise and a pressure release signal Uprelease are subsequently supplied to the pressure applying means 4', corresponding to said computed pressure P2 and delay time Tdelay1. The delay time Tdelay and the pressure P for the pressure applying means 4' are refined by repeating this measurement a limited number of cycles. The comparison of the first time duration ΔT1 with the second time duration ΔT2 is repeated until the point in time at which the opening of the artery coincides within a predetermined tolerance time interval with the point in time at which the maximum pressure occurs. The pressure determined in the pressure applying means 4' at this moment gives an accurate indication of the systolic blood pressure S. Said means 11 for computing determine the pressure-time profile according to which said pressure is released, said means 11 for computing supplying the pressure release signal Uprelease corresponding to said profile. As can be seen from this Figure, the adjustment of the pressure-time profile according to which said pressure in the pressure applying means 4 is released also renders it possible to achieve an accurate measurement in a limited number of cycles.

FIG. 3b shows the diagram of the measurement of FIG. 3a after a limited number of cycles. Accurate measurement of the systolic blood pressure S is achieved after this limited number of cycles. This is done by adjusting the delay time after which the pressure is to be released in accordance with computed next values for Tdelay1, or by adjusting the pressure as applied by the pressure applying means 4' to the artery in accordance with computed next values for P2. It is noted that it is possible to adjust the pressure or the delay time, or to adjust both, depending on the calculations.

FIG. 4 shows a diagram of a measurement of the diastolic blood pressure with the system of FIG. 1 in a further measuring step. A heart rate duration ΔThr from the reference point in time b to the end point in time f is determined from the timing of at least two heart beats of the subject. The heart rate duration ΔThr and a third time duration ΔT3 from the reference point in time to a further point in time e at which an opening of the artery occurs, are compared, from which comparison is computed a second delay time Tdelay2 from said reference point in time b after which a next pressure release signal is to be supplied to said pressure applying means. Subsequently, a second pressure release signal Uprelease2 corresponding to said computed second delay time Tdelay2 is supplied to said pressure applying means 4'. The delay time for the pressure applying means 4' is refined by repeating this measurement a limited number of cycles. The comparison of the heart rate duration ΔThr with the third time duration ΔT3 is thus repeated until the point in time at which the opening of the artery coincides within a predetermined tolerance time interval with the point in time at which one heart rate duration reaches its end, and thus a minimum blood pressure occurs. The pressure determined in the pressure applying means at this moment gives an accurate indication of the diastolic blood pressure D of the subject.

What is claimed is:

1. A system (1) for measuring blood pressure during a limited number of blood pressure cycles at an area (2) overlying an artery (3) of a living subject, comprising:
    means (4) for applying a pressure (P) to the artery for occluding said artery in response to a pressure signal (Uprise), and for subsequently releasing said pressure to re-open said artery in response to a pressure release signal (Uprelease);
    means (5) for determining a reference point in time (b), and for providing a reference time signal (Uref) corresponding to said reference point in time (b);
    means (6) for detecting a first point in time (c) at which a maximum pressure occurs during a blood pressure cycle, and for
        providing a first time signal (Umax) corresponding to said first point in time (c);
    means (7) for computing, from the reference time signal (Uref) and the first time signal (Umax),
        a first time duration (ΔT1) from the reference point in time (b) to the first point in time (c);
    means (8) for detecting a second point in time (d) at which an opening of the artery occurs after the release of said pressure, and for
        providing a second time signal (Uopen1) corresponding to said second point in time (d);
    means (9) for determining the pressure in said means (4) for applying pressure to the artery, at the second point in time (d);
    means (10) for computing, from the reference time signal (Uref) and the second time signal (Uopen1),
        a second time duration (ΔT2) from the reference point in time (b) to the second point in time (d);
    means (11) for computing, by comparing the first time duration (ΔTI) with the second time duration (ΔT2),
        a delay time (Tdelay1) from said reference point in time (b) after which a next pressure release signal is to be supplied to said means (4) for applying a pressure, and for computing a pressure (P2) to be applied to said artery in a next measuring cycle, and for supplying subsequently a pressure signal (Uprise) and a pressure release signal (Uprelease) corresponding to said computed pressure (P2) and delay time (Tdelay1) to said means (4) for applying a pressure.

2. A system as claimed in claim 1, characterized in that the reference point in time (b) is a point in time at which a start of a systolic phase in a blood pressure cycle occurs.

3. A system as claimed in claim 2, characterized in that the means (5) for detecting the start of said systolic phase comprise a sensor for detecting during operation a point in time at which a pressure pulse (14) in the means (4) for applying a pressure to the artery rises above a predetermined threshold value (15).

4. A system as claimed in claim 1, characterized in that in the system (1) comprises:
    said means (11) for computing, which are furthermore designed for determining a further delay time (Tdelay2) from said reference point in time (b) after which a further pressure release signal is to be supplied to said means (4) for applying a pressure in a next measuring step for measuring the diastolic blood pressure, and for supplying a further pressure release signal (Uprelease2) corresponding to said further delay time (Tdelay2);
    means (12) for determining, from the timing of at least two heart beats of the subject, a heart rate duration (ΔThr) from the reference point in time (b) to an end point in time (f) corresponding to an end of one pressure cycle;
    means (8) for detecting a further point in time (e) at which an opening of the artery occurs after the release of said pressure in response to said further pressure release signal (Uprelease2), and for
        providing a third time signal (Uopen2) corresponding to said further point in time;
    means (24) for computing, from the reference time signal (Uref) and the further time signal (Uopen2),
        a third time duration (ΔT3) from the reference point in time (b) to the further point in time (e);
    said means (11) for computing further determining, by comparing the heart rate duration (ΔThr) and the third time duration (ΔT3),
        a next value for said further delay time (Tdelay2) after which a next pressure release signal is to be supplied to said means (4) for applying a pressure in said next measuring step, and for
        supplying subsequently a next value for said further pressure release signal (Uprelease2) corresponding to said next value for said further delay time (Tdelay2) to said means (4) for applying a pressure.

5. A system as claimed in claim 1, characterized in that said means (6) for detecting said first point in time (c) comprise a pressure sensor (26) for measuring a pressure in the means (4) for applying a pressure to the artery (3) during operation, and a processor (36) for determining said first point in time from a signal provided by the pressure sensor.

6. A system as claimed in claim 1, characterized in that the means (8) for detecting said second point in time (d) comprise an electro-optical sensor (28) for detecting the presence of blood in the artery and a further processor (38) for determining said second point in time from a signal provided by the electro-optical sensor (28).

7. A system as claimed in claim 1, characterized in that said means (11) for computing also determine a pressure-time profile according to which said pressure is released, said means (11) for computing supplying a pressure release signal (Uprelease) corresponding to said profile.

* * * * *